United States Patent [19]
Evans et al.

[11] Patent Number: 5,261,538
[45] Date of Patent: Nov. 16, 1993

[54] AEROSOL TESTING METHOD

[75] Inventors: Rix E. Evans, Wendell; Alec P. Flowers, Jr., Raleigh; David E. Hockaday, Wilson; David W. Loar, Raleigh; James K. Proctor, Nashville, all of N.C.

[73] Assignee: Glaxo Inc., Research Triangle Park, N.C.

[21] Appl. No.: 871,873

[22] Filed: Apr. 21, 1992

[51] Int. Cl.$^5$ .................. B07C 5/16; G01N 25/00
[52] U.S. Cl. ........................ 209/2; 209/523; 209/552; 374/45
[58] Field of Search ............ 209/592, 522, 523, 2, 209/552; 374/45

[56] References Cited

FOREIGN PATENT DOCUMENTS

| | | | |
|---|---|---|---|
| 1-29150 | 5/1989 | Japan | 374/45 |
| 3-22047 | 9/1991 | Japan | 374/45 |
| 911232 | 3/1982 | U.S.S.R. | 374/45 |
| 1029083 | 7/1983 | U.S.S.R. | 374/45 |
| 1191803 | 11/1985 | U.S.S.R. | 374/45 |
| 1314270 | 5/1987 | U.S.S.R. | 374/45 |

OTHER PUBLICATIONS

P. Byron, Respiratory Drug Delivery, CRC Press, Boca Raton Fla. (1990), pp. 168-205.
W. Moore, Physical Chemistry, 3rd Ed., Chap. 4, Prentice-Hall, Englewood Cliffs, N.J. (1963) pp. 95-109.
J. Holman, et al., Experimental Methods for Engineers, §7—7, McGraw-Hill, N.Y. (1978) pp. 235-239.
Hot Wire/Hot Film Anemometry Probes & Accessories, TSI, Inc., St. Paul Minn. (1988).

Primary Examiner—Robert P. Olszewski
Assistant Examiner—Steven M. Reiss
Attorney, Agent, or Firm—Charles T. Joyner

[57] ABSTRACT

The present invention comprises a method for measuring the amount, i.e., mass, of a volatile liquid which comprises passing the mass over a heat loss measuring device, calculating the amount of heat loss accompanying the vaporization of the mass and correlating the heat loss to measurement of heat loss of known liquid aerosol mass made with the same device.

7 Claims, 2 Drawing Sheets

AEROSOL TESTING METHOD

This invention relates to a method of measuring the mass of an aerosol formulation delivered from a container after activation of a metered dose valve.

BACKGROUND OF THE INVENTION

Drugs for treating respiratory and nasal disorders are frequently administered in aerosol formulations through the mouth or nose. One widely used method for dispensing such aerosol drug formulations involves making a suspension formulation of the drug as a finely divided powder in a liquefied gas known as a propellant. The suspension is stored in a sealed container capable of withstanding the pressure required to maintain the propellant as a liquid. The suspension is dispensed by activation of a dose metering valve affixed to the container.

A metering valve may be designed to consistently release a fixed, predetermined mass of the drug formulation upon each activation. As the suspension is forced from the container through the dose metering valve by the high vapor pressure of the propellant, the propellant rapidly vaporizes, i.e., boils, leaving a fast moving cloud of very fine particles of the drug formulation. This cloud is usually directed into the nose or mouth of the patient by a channeling device, e.g., a cylinder like or cone-like passage, with one of its ends attached to the outlet of the pressurized container, and the other end inserted in the mouth or nose of the patient. Concurrently with the activation of the aerosol dose metering valve, the patient inhales the drug formulation particles into the lungs of nasal cavity. Systems for dispensing drugs in this way are known as "metered dose inhalers" (MDI's). See Peter Byron, *Respiratory Drug Delivery*, CRC Press, Boca Raton, Fla. 1990 for a general background on this form of therapy.

Patients often rely on medication delivered by MDI's for rapid treatment of respiratory disorders which are debilitating and, in some cases, even life threatening. Therefore, it is essential that the prescribed dose of aerosol medication delivered to the patient consistently meet the specifications claimed by the manufacturer and comply with the requirements set forth by drug regulatory authorities such as the FDA. Thus, testing of MDI units for proper drug delivery by the metering dose valve is a part of the manufacturer's quality assurance procedure.

One conventional method to test delivery of MDI's consists of taring each MDI and measuring the weight lost after the delivery of one dose. This method is accurate and adequate for testing a small number of samples. However, it is poorly suited for high speed production and packaging of MDI's.

A common method of testing drug delivery utilizes indirect pressure decay after activation of each MDI. This method does not render a direct mass measurement, but rather an approximation based upon the force exerted indirectly by the superheated vapor on a pressure transducer. As a consequence, this method is unable to detect MDI's which are marginally out of tolerance. Further, unacceptable inaccuracies result unless the production rate is less than about one and a half MDI's per second which is significantly below the optimal production rate. Therefore, multiple testing stations are used in the MDI production line leading to an increased maintenance burden and validation complications.

Thus, the manufacturer of MDI's is faced with a choice of i) testing each MDI and reducing the production speed to less than 1 and a half per second or ii) installing multiple testing machines in the production line. This dilemma has lead to a search for a method of accurately measuring the delivery of each MDI without sacrifice of production speed.

SUMMARY OF THE INVENTION

The present invention comprises a method for measuring the amount, i.e., mass, of a volatile liquid which comprises passing the mass over a heat loss measuring device, calculating the amount of heat loss accompanying the vaporization of the mass and correlating the heat loss to measurement of heat loss of known liquid aerosol mass made with the same device.

A particularly useful application of this method is the measurement of the mass of an aerosol propellant, delivered upon activation of a metering valve attached to a vessel containing an aerosol product. This method is well suited as a quality assurance procedure in the production of metered dose inhalers (MDI's) because it can be used to measure delivery from a metering valve for each MDI with acceptable accuracy and precision without slowing production. The second aspect of the present invention is a method of quality assurance in the manufacturing of metered dose inhalers using the present method of measuring the mass of a liquid aerosol formulation.

DETAILED DESCRIPTION OF THE INVENTION

Figure 1:
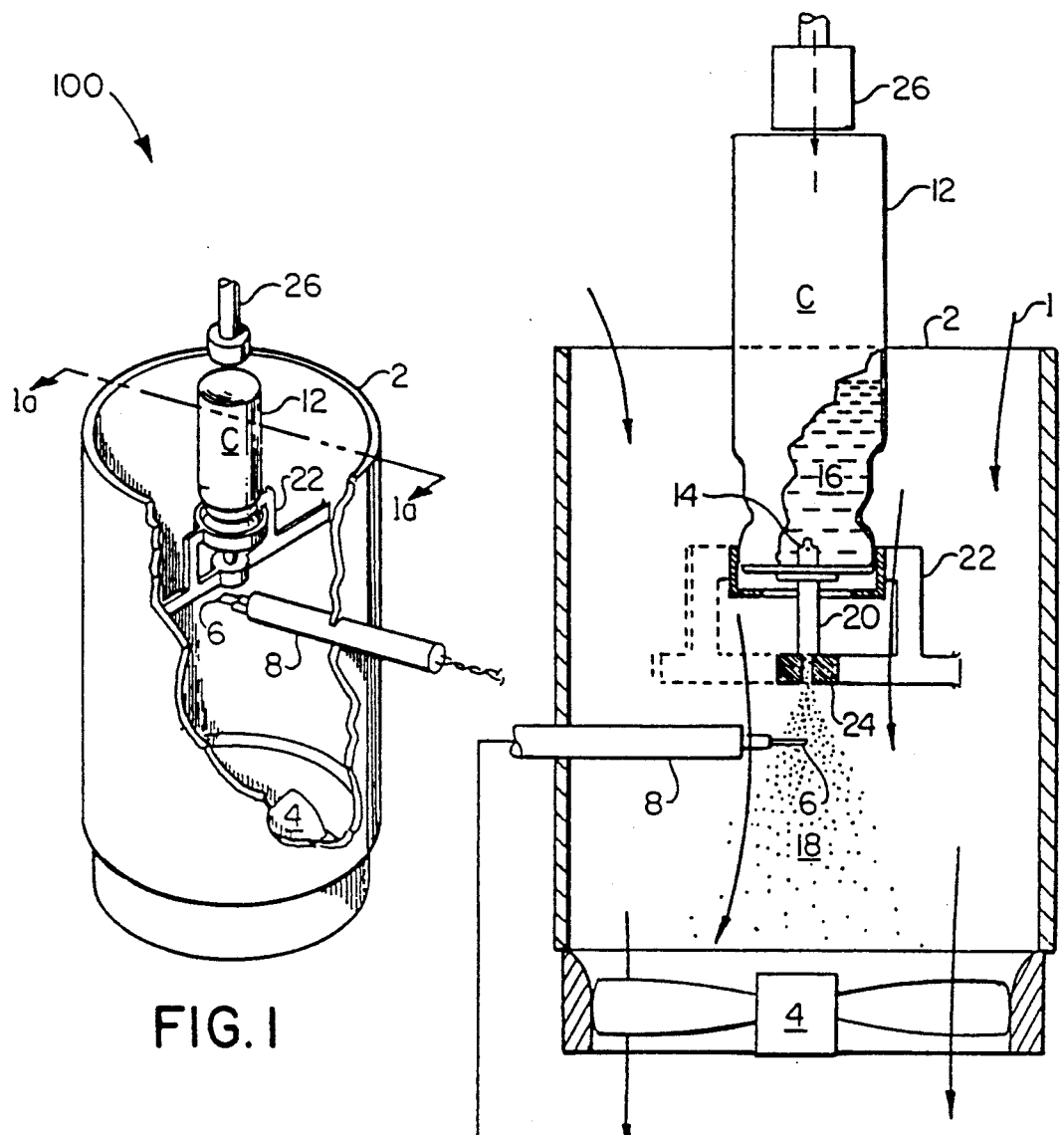
FIG. 1 depicts a perspective view of a testing apparatus for carrying out the method of the invention.

The transition from liquid state to gaseous state is achieved through the isothermal process know as "evaporation", or "boiling" if the process is rapid. An isothermal process is one that occurs at a constant temperature. As heat is applied to a liquid the temperature will rise proportionately until it reaches the boiling point. Once at the boiling point, as heat is applied the liquid changes to the gaseous state but the temperature remains constant. Thus, the heat energy being applied is the energy required to transform the liquid into a gas or vapor and is known as the "latent heat of vaporization." In effect, for a liquid to change to a gas at its boiling point, it must extract heat from its environment. A discussion of the phenomenon of latent heat of vaporization can be found in standard text books on physical chemistry, e.g. W. Moore, *Physical Chemistry*, 3rd Ed., Chap. 4, Prentice-Hall (1963).

When a liquid is released from a sealed container, the liquid extracts heat from its environment, e.g., the surrounding air, to evaporate. The extraction of heat from the liquid's surrounding results in a lowering of the temperature of those surroundings. When a volatile liquid, i.e., a liquid with a boiling point below or slightly above ambient temperature, is released into the air as a fine spray at ambient temperature, the evaporation is very rapid and the consequential cooling of the air is observable even to the touch.

The propellants used in aerosol dispensers are highly volatile liquids with boiling points well below ambient temperature. For example, at atmospheric pressure, dichlorodifluoromethane, also known as "propellant 12" and "P12," has a boiling point of $-29.8°$ C. and 1,1,1,2-tetrafluoroethane, also known as "propellant 134a" and "P134a," has a boiling point of $--26.5°$ C. When the valve of a propelled aerosol dispenser is activated, the released propellant very rapidly evaporates to produce the aerosol, i.e., a fine suspension of the aerosol formulation in air and vaporized propellant. The rapid evaporation of the propellant extracts heat from the surrounding air producing a significant cooling effect.

In the method of the present invention, a mass of a volatile liquid to be measured is discharged into a constant temperature and constant flow air stream and onto the probe of a heat loss measuring device placed downstream from the point of discharge. The cooling effect of the vaporization of the liquid is sensed as a transient loss of heat from the area surrounding the probe and recorded as a transient reduction of temperature of the air stream. Two or more different, known masses of the same liquid are discharged under identical conditions and the corresponding reduction in temperature recorded. The mass of the sample is determined by correlating the reduction in temperature resulting from its discharge with reduction in temperature caused by discharge of the samples of known mass. Thus, the mass of the discharged volatile liquid is calculated as a function of the latent heat of vaporization of the liquid.

If the volatile liquid is a propellant being used to disperse a drug formulation from an MDI, the amount of formulation discharged with each valve activation is directly and consistently proportional to the mass of the propellant discharged. That is, knowledge of the mass of propellant discharged from an aerosol dispenser, an MDI, can be directly interpreted as knowledge of the amount of drug formulation dispensed. This knowledge is particularly important for quality assurance procedures in the manufacturing of MDI's and is discussed in detail hereinbelow.

It is preferable in the present method of measuring mass that temperature and flow rate of the air stream be kept constant from measurement to measurement. Therefore, it is convenient to practice the present method within a partially enclosed chamber, i.e., a test chamber, wherein temperature and flow rate can be controlled and isolated from extraneous air currents, e.g., by means of enclosure within a tube having uniform cross section.

Figure 1A:
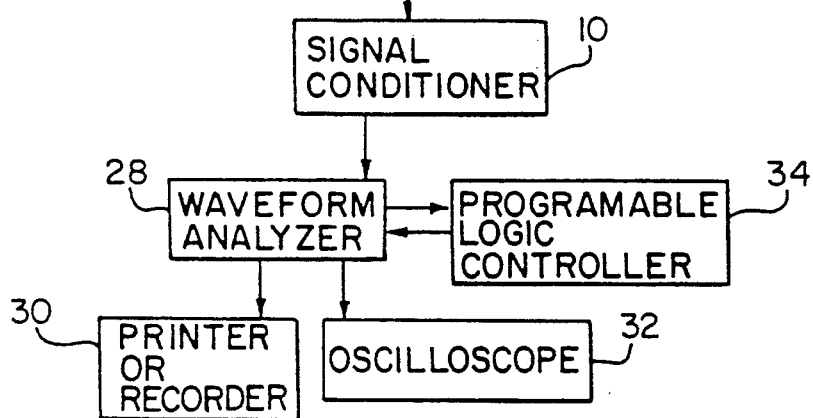
FIG. 1a is an elevational cross section of the apparatus with a schematic diagram of the electrical connection for the generated signal.

In FIGS. 1 and 1a an apparatus 100 is provided to measure the mass of an aerosol. A constant air flow 1 is maintained through the test chamber 2. The dimensions of the test chamber are not critical, but must be sufficient to allow a constant air flow through the chamber while preventing extraneous air flow from the surroundings of the chamber. The constant air flow may be generated by an air moving means such as a motorized fan 4 placed i) in close proximity to the exit of the test chamber as depicted in FIG. 1 and 1a, ii) close proximity to the entrance of the test chamber or iii) remotely located and connected by a duct to either the entrance or exit.

With a constant flow of air through the test chamber a baseline condition is established across sensing portion 6 of the probe of a heat loss measuring device 8, e.g., a hot film or hot wire anemometer, and is set as the reference condition, e.g., by a signal conditioner (SC) 10. The SC 10 converts minute changes in the current required to maintain a predetermined temperature at the probe sensing portion 6 to an analog voltage (0-5 VDC). A decrease in temperature at the probe sensing portion 6 results in an increase in current required to maintain the wire or metallic film at the predetermined temperature. The SC 10 also acts as a filter by averaging input signal to essentially eliminate electrical "noise" and provide a "clean," linear signal.

A vessel 12 equipped with a metering dose valve 14 and containing a liquid aerosol propellant 16 is mounted in the test chamber 2 in an orientation whereby i) the discharge of propellant upon activation of the metering valve 14 is in the direction of the air flow 1 and ii) the discharge 18 directly impinges on the sensing portion 6 of the probe of a heat loss measuring device 8 as shown in FIG. 1a. The discharge tube 20 which extends from the metering dose valve 14, is positioned by the vessel holder 22 in a fixed position against the opening in support ring 24 of the vessel holder 22. The metering valve 14 may be activated by placing pressure against the end of the vessel 12 opposite from the metering valve 14. The pressure forces the discharge tube 20 into the vessel 12 activating the metering dose valve 14. Such pressure may be applied manually or mechanically, e.g. by mean of a plunger 26 connected to an electrical, pneumatic or other means to move the plunger against the vessel 12.

The signal generated by the probe of the heat loss measuring device 8 is electronically and mathematically processed and compared to the cooling resulting form the discharges of the same liquid aerosol propellant under the same conditions by the waveform analyzer 28. The processed signal is transmitted to a printer or recorder 30 where it is graphically recorded, and simultaneously transmitted to an oscilloscope 32 for rapid visualization. The processed signal may also be further processed electronically and mathematically, e.g., by a programmable logic controller, 34, to actuate devices which can reject from the production run those aerosol vessels with valves delivering drug formulation above or below the tolerated range.

The heat loss measuring device suitable for use in this invention should preferably: i) respond within 10 milliseconds to a temperature change, ii) be sensitive enough to sense changes of less than about $0.01°$ C., iii) have an operational range from about $10°$ C. to about $40°$ C. with recovery to a baseline setting within 50 milliseconds and iv) be capable of producing an electrical signal which can be amplified, processed, recorded and viewed with conventional electronic components available to control and monitor manufacturing processes.

The temperature sensing probe and related signal processing equipment used in the art of hot wire and hot film anemometry fulfills these requirements and is well suited to the present invention. Anemometry employs a probe tipped by a heated, fine wire which is connected to a bridge circuit. In turn, the bridge circuit is connected to an electronic amplifier which is connected to a device for visualizing the change of electrical signal, such as a recorder or oscilloscope. A change in temperature of the hot wire alters its electrical resistance which unbalances the bridge circuit to generate an electrical signal proportional to the change of temperature of the wire. The electrical signal may then be amplified, electronically and mathematically processed and presented in a useful, graphic form. In some applications a very small, heated, insulated cylinder bearing a thin metallic film is used in lieu of the hot wire. For the method of this invention either a hot wire or hot film probe is acceptable and any reference hereinafter to either should be taken as including both.

In the art of anemometry, the hot wire probe and the related circuitry is used to measure the flow of air or gases by measuring the cooling of the hot wire when it is placed in the flow. That is, the cooling effect is correlated to the rate of flow. Thus, the hot wire anemometry system is essentially used as a sophisticated, electronic thermometer. The theory and practice of hot wire/hot film anemometry is taught in *Experimental Methods for Engineers*, J. Holman and W. Gajda, Jr., § 7—7, McGraw-Hill, New York (1978). Further information, including specifications of anemometry equipment offered for sale, is found in the brochure, "Hot Wire/Hot Film Anemometry Probes & Accessories," (1988) by TSI Incorporated, St. Paul, Minn.

Aerosol vessels containing drug formulations such as MDI's may be sequentially subjected to the method of this invention by conventional mechanical means known in the art. Further, those skilled in the art of manufacturing aerosol formulations will appreciate that some variation in the method taught above may be required to optimize the results.

The magnitude of temperature reduction and the duration of such reduction at the sensing part of the probe is directly proportional to the mass of the propellant discharged. Therefore, the electronic signal from the probe, processed by the signal conditioner and waveform analyzer and graphically displayed by the printer or recorder (or displayed on the oscilloscope) is also directly proportional to the mass of the propellant discharged.

Figure 2A:
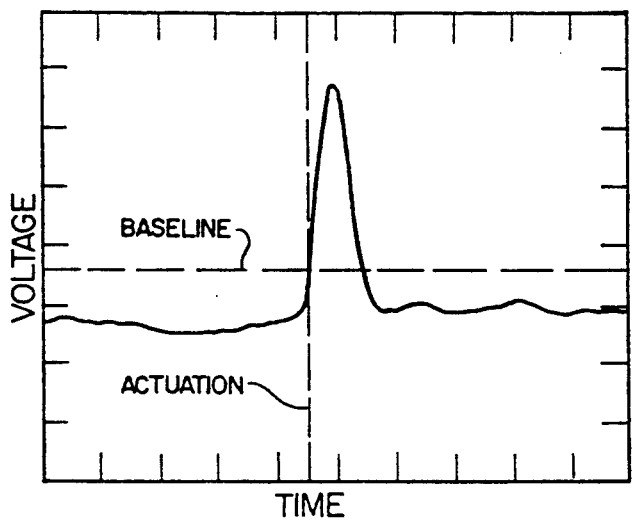
FIGS. 2a, 2b and 2c are oscilloscope wave traces from testing mass according to the invention where the masses are within tolerable limits, too low and too high, respectively.
Figure 2B:
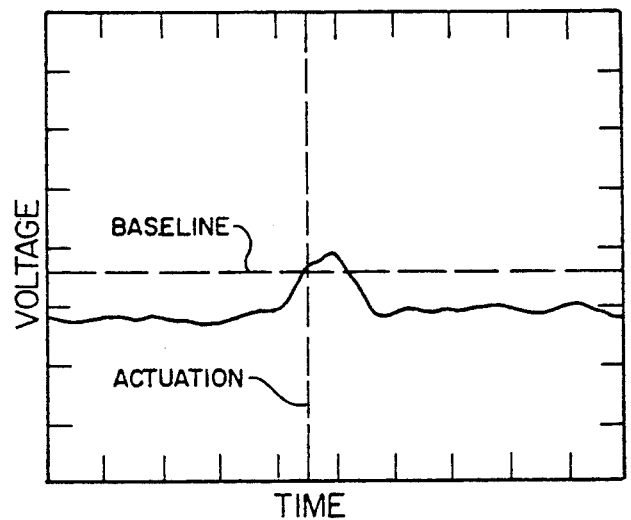
Figure 2C:
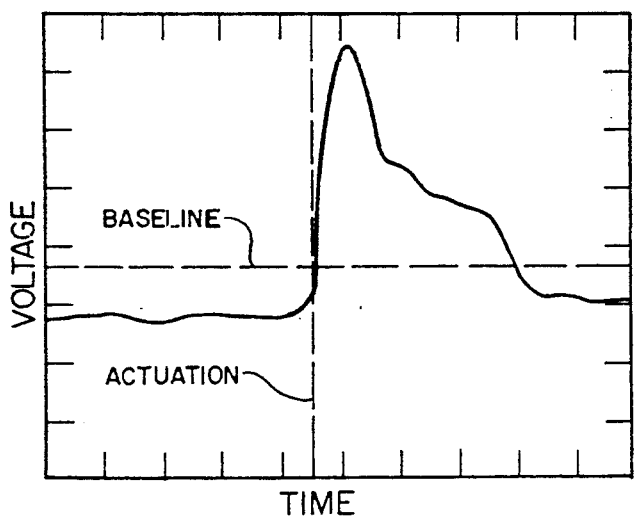

FIGS. 2a, 2b and 2c depict graphs of the level of the electronic signal (voltage) in relation to duration as as would be displayed by the printer or recorder on the oscilloscope screen. The area under the curve in each of the three graphs is directly proportional to the mass of the propellant discharged and, hence, the transient temperature reduction at the probe. FIG. 2a shows the pattern produced by discharge of propellant through a normal valve. FIG. 2b is a corresponding graph produced by a valve which discharges an unacceptably low amount of propellant while FIG. 2c is produced by a valve which does not close properly after activation and, thus, discharges an excessive amount of propellant.

Two or more known masses of propellant can be sequentially discharged into a constant air flow onto the probe in the test chamber to establish a series of corresponding standardized graphs. An unknown mass of propellant may then be discharged and the area under the curve in the resulting graph is compared and correlated to the area under the curves produced by the discharges of the standard masses.

The present method of measuring mass of aerosol propellant may be adapted as a method of quality assurance in the manufacture of MDI's which comprise the following steps:

a) determining the mass of the output of an MDI by the method described above, b) rejecting those MDI's which have output below or above a predetermined range of tolerance.

In particular when the above method of quality assurance is adapted for continuous production run the following detailed steps would be appropriate:

a. Placing each MDI sample from a production run into a test chamber as depicted in FIGS. 1 and 1a., b. Activating the metering valve of the sample MDI from a position fixed in relation to the sensing portion of a hot wire or hot film anemometer probe as depicted in FIGS. 1. and 1a, c. Recording the temperature reduction and the duration of the reduction, d. Comparing the temperature reduction recorded in step c. with that produced under the same conditions by an essentially identical MDI containing the same formulation, but having a known mass of output upon activation, i.e., a "standardized MDI".

e. Removing the sample MDI from the test chamber and,

1. Placing it back on the production line if the output mass is within the predetermined tolerances in relation to the output mass of the standardized MDI, or
2. Discarding the sample MDI if the output mass is above or below the predetermined tolerances in relation to the output mass of the standardized MDI.

The method of this invention may be adapted to test a wide variety of metered valve aerosol dispensers which use liquid propellants. It is particularly useful in the quality assurance of MDI's employed to deliver respiratory drugs. For example, this method may be used for quality assurance in the production of MDI's containing the respiratory drugs albuterol, salmeterol, amiloride, fluticasone esters and beclomethasone esters.

Suitable liquids which can be measured by the present invention as aerosols include, but are not limited to, dichlorodifluoromethane, 1,1,1,2-tetrafluoroethane, heptafluoropropane, tetrachlorofluoroethane, butane, isobutane and propane.

The following example illustrate this invention but should not be construed as a limitation thereof. The symbols and conventions used in these examples are consistent with those used in contemporary engineering literature.

A standardized MDI containing a suspension of albuterol in P12 is placed into an apparatus essentially as depicted in FIGS. 1 and 1a with the tip of the discharge tube about 30 mm from the sensing portion of a TSI model 1210-T1.5 hot wire anemometer probe supplied by TSI Incorporated. A constant air flow of about 20 cfm to about 30 cfm is maintained through the test chamber by a tubeaxial fan supplied by Radio Shack.

The signal from the anemometer is transmitted by coaxial, shielded cable (CSC) to a model 157 internally installed signal conditioner supplied by TSI, Inc. The conditioned signal is then transmitted by CSC to a model 170 Gould waveform analyzer supplied by General Electric Instruments, Inc. The waveform analyzer transmits a signal by CSC to a chart recorder or a high speed printer and simultaneously by CSC to a model 4073 Gould digital storage oscilloscope supplied by General Electric Instruments, Inc. The signal from the waveform analyzer is also transmitted to an Allen-Bradley, Family 5, programmable logic controller. With the constant air flow through the test chamber the signal form the anemometer is set as the baseline condition.

A standard MDI, the output of which has been previously measured by taring and measuring the weight lost after a discharge, is activated by a downward thrust of the plunger. The resulting temperature drop sensed by the anemometer is recorded electronically in the signal conditioner as the standard. Preferably the output of two or more standardized MDI's are recorded and electronically and mathematically averaged in the signal conditioner to set the standard.

Alternatively, the outputs of two or more MDI's (previously found have different outputs) may be correlated with the corresponding drop in temperature upon discharge. Such correlation may conveniently be done electronically and mathematically in the signal conditioner to yield a standard curve relating mass of output to resulting temperature drop. The mass of the output of an MDI being tested can be determined by relating the temperature drop resulting from its discharge to the corresponding output mass on the standard curve.

The standardized MDI is removed and MDI's from the production run to be tested are sequentially placed in the test chamber and activated in the same way as was the standardized MDI. The signal generated by the anemometer as a result of the temperature reduction about the probe upon discharge of each MDI is electronically and mathematically compared with the signal previously generated by one or more standardized MDI's. If the signal generated by discharge of a sample MDI is outside the preset tolerance, a signal is transmitted to the Allen-Bradley programmable logic controller which, in turn, activates a means to remove the out-of-tolerance MDI from the production run.

The output of an MDI being tested can be observed within 300 miliseconds on the oscilloscope. This rapid, visual indication of the outputs of the production run MDI's is useful to the production line operator in spotting defect trends and detecting substandard lot of MDI valves. A permanent record can be made with the recorder or printer.

We claim:

1. A method of measuring the mass of a volatile liquid in the form of an aerosol which comprises, 1) passing said aerosol over a heat loss measuring device, 2) measuring the amount of heat loss due to vaporization of said aerosol and 3) correlating said measurement to heat loss measurements of known masses of said liquid with said device under essentially identical condition.

2. The method of claim 1 wherein the volatile liquid is an aerosol propellant.

3. The method of claim 2, wherein said aerosol propellant is dichlorodifluroromethane, 1,1,1,2-tetrafluoroethane, heptafluoropropane, tetrachlorotetrafluoroethane, butane, isobutane or propane.

4. The method of claim 1 wherein the heat loss device is a hot film or hot wire anomometer.

5. The method of claim 1 wherein the volatile liquid is discharged from an aerosol container equipped with a metering dose valve.

6. A method of quality assurance in the manufacturing of metered dose inhalers comprising:
   a) determining the mass of the output of a sample metered dose inhaler by the method of measuring the mass of a volatile liquid in the form of an aerosol comprising, 1) passing said aerosol over a heat loss measuring device, 2) measuring the amount of heat loss due to vaporization of said aerosol and 3) correlating said measurement to heat loss measurements of known masses of said liquid with said device under essentially identical condition and
   b) rejecting those metered dose inhalers which have output below or above a predetermined range of tolerance.

7. The method of claim 6 wherein said metered dose inhalers contain an aerosol formulation of albuterol, salmeterol, amiloride, a fluticasone ester or a beclomethasone ester

* * * * *